United States Patent

Palomo-Coll et al.

[11] Patent Number: 4,481,357
[45] Date of Patent: Nov. 6, 1984

[54] PROCESS FOR THE PREPARATION OF 3-SUBSTITUTED 7-AMINOCEPHALOSPORANIC ACIDS

[75] Inventors: Alberto Palomo-Coll; Antonio L. Palomo-Coll, both of Barcelona, Spain

[73] Assignee: Gema, S.A., Barcelona, Spain

[21] Appl. No.: 410,932

[22] Filed: Aug. 24, 1982

Related U.S. Application Data

[63] Continuation-in-part of Ser. No. 393,423, Jun. 29, 1982.

[30] Foreign Application Priority Data

Sep. 1, 1981 [ES] Spain ................................ 505.092

[51] Int. Cl.³ ................... C07D 501/18; A61K 31/545
[52] U.S. Cl. ........................................ 544/016; 544/26; 544/27; 544/21; 544/29; 260/245.2 R; 260/245.3
[58] Field of Search ...................... 260/245.2 R, 245.3, 260/245.2 T; 424/270, 271; 544/16, 26, 29, 21

[56] References Cited

U.S. PATENT DOCUMENTS

4,312,986  1/1982  Saikawa et al. .................... 544/27

Primary Examiner—Nicholas S. Rizzo
Attorney, Agent, or Firm—Scully, Scott, Murphy & Presser

[57] ABSTRACT

A 3-substituted 7-aminocephalosporanic acid of formula:

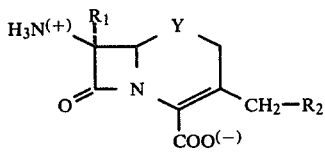

where $R_1$ is hydrogen, methyl of methoxy, Y is nitrogen, oxygen sulphur or a sulphoxide group, $R_2$ is a group selected from among azide or from a radical having the formula $R_3$—S— where $R_3$ may be, among others, alkyl, aliphatic acyl, methyl and chlorine or methoxy substituted aromatic acyl, is prepared. A compound of formula

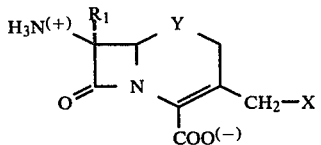

(X being chlorine, carbamoyloxy or acetoxy) is added to a medium constituted by water, a compound which may be nitric acid or a compound of formula $R_3$—SH and a tertiary organic base. With a reaction isoelectric pH regulator, the mixture takes on a specific process pH analytical profile, the compounds of said mixture being reacted together at particular temperatures and with a specific process time.

1 Claim, 1 Drawing Figure

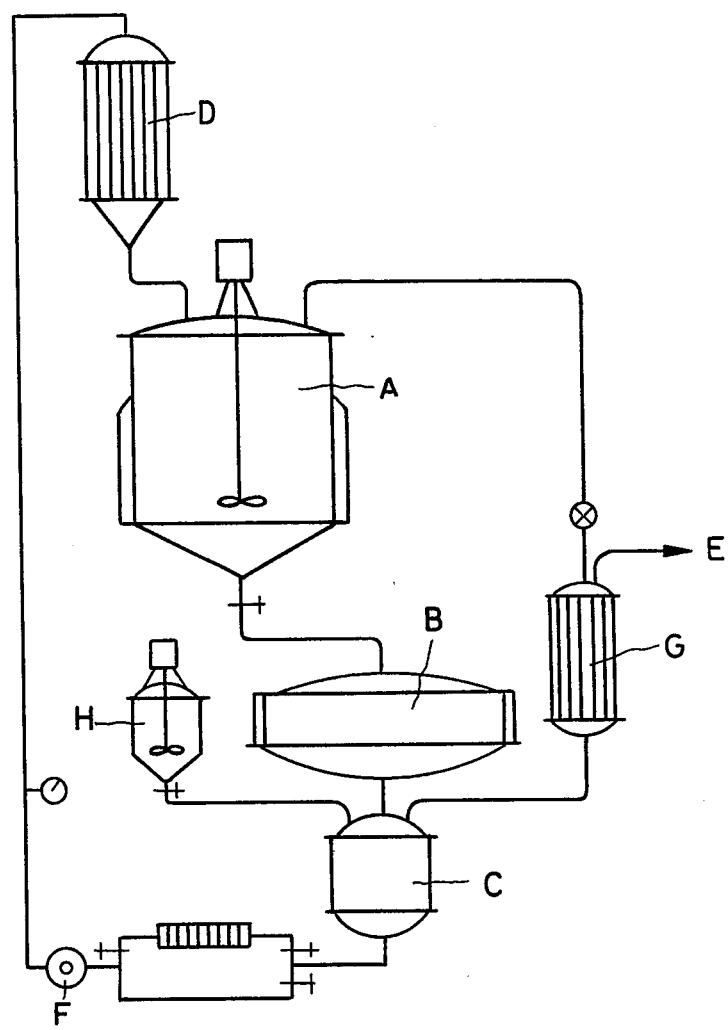

PROCESS FOR THE PREPARATION OF 3-SUBSTITUTED 7-AMINOCEPHALOSPORANIC ACIDS

This application is a continuation-in-part of application Ser. No. 393,423 filed June 29, 1982.

FIELD OF THE INVENTION

This invention relates to a process for the preparation of 3-substituted 7-aminocephalosporanic acids which are of interest for the production of antibiotics of the cephalosporin and cephamycin group, such antibiotics being applicable in human and veterinary medicine.

DESCRIPTION OF THE PRIOR ART

There is described in the scientific and technical literature the reaction of a compound having the thiol (mercapto) functional group, in salt form, with the acetoxymethyl group in the 3-position of a 7-aminocephalosporanic acid derivative, to substitute the acetoxy group in that position. Examples of the foregoing are disclosed in the U.S. Pat. No. 3,516,997, and Japanese application No. 154.287/75, British application No. 1,319,173 and German application Nos. 1.795.484, 2.018.600 and 2.065.621. These publications specify that it is desirable to effect the reaction in water or in a mixture of water and organic solvent with the pH held to 6–7. Nevertheless, even under these reaction conditions which are considered to be the preferred ones, the product obtained is extraordinarily impure and is isolated with yields of from 35 to 50% at the most.

For ready conversion in the 3 position, using 7-amino-3-acetoxymethylcephalosporanic acid as starting product, it has been alleged that it is desirable to protect the amino group by acylation and to effect the reaction in an aqueous medium or in a mixture of water and organic solvent, with an almost neutral pH. Examples of the foregoing are Japanese patent application Nos. 295/74, 10.077/73 and Japanese published patent application No. 13.023/71 and in U.S. Pat. No. 3,840,531 and German Pat. No. 2.332.045. To facilitate the conversion of the acetoxy group, the reaction has been described as being effected in the presence of inorganic salts such as KI, NaI-CaI$_2$, BaI$_2$, NaCl and the like, see, for example, British Pat. No. 1,040,804 and Japanese patent application No. 95.088/76. Generally speaking, under these conditions, the yields obtained are said to be around 60% to 80%. Nevertheless, the method is complicated because it is necessary (1) to acylate and isolate the 7-aminocephalosporanic acid, (2) substitute the acetoxy group and (3) eliminate the acyl group to release the 3-substituted 7-aminocephalosporanic acid.

In Spanish Pat. No. 482.252 (Japanese patent application No. 82.377/78), the reaction of the 7-aminocephalosporanic acid, or derivatives thereof with substitution in the 4 position carboxyl, such as esters, anhydrides and amides, or in the 7-amino group, among which are the acyl derivatives, with a thiol is effected exclusively in an organic solvent, preferably the nitriles, nitroalkanes and carboxylic acids among others, in the presence of a strong protonic acid. The only yields expressed with 7-aminocephalosporanic acid and 2-mercapto-1-methyl-1H-tetrazole vary from 76% to 87.7%. Generally speaking, this process has the drawback of a loss of organic solvent, which product increases the production cost, like those which recite the use of mixtures of water with a high proportion of organic solvent. There are also limitations with respect to the substituent, for example in the case of the azido group (N$_3^-$) and, of course, with the 4 position carboxyl derivatives, which require a later unblocking treatment of such function. There are also difficulties and limitations of solubility in the organic solvent.

In the nucleophilic substitution reaction of the acetoxy group in 7-aminocephalosporanic acid, Cocker et al. (J. Chem. Soc., 1965, 5023) showed that with relatively high concentrations at room temperature, there is formed a by-product of the condensation of the 7-aminocephalosporanic acid with itself, similar to the one obtained in the absence of the nucleophilic agent. They also showed (ibidem, p. 5031) that the cephalosporin is decarboxylated with N-acyl-7-aminocephalosporanic acid and the nucleophilic reactant at 50° C., and that in the case of the reaction with sodium azide, it reaches from 3.8 to 13.6% of the said decomposition.

The present inventors have also observed that at room temperature 44% of a 4.5% triethylamine salt of 7-aminocephalosporanic acid is quickly destroyed. When held at 70° C. for 60 minutes, both in the presence and in the absence of a thiol compound, the destruction was total. They have also confirmed that similar decompositions, occur at pH 7.6 with a 9% concentration at room temperature over a period of from 24 to 70 hours and that the effect is accelerated by a temperature increase.

DeMarinis et al. (J. Medicinal Chem., 19, 758, 1976) describe the general process for the preparation of 7-amino-3-[(heterocyclo)thiomethyl]-3-cephem-4-carboxylic acids by reaction of the 7-aminocephalosporanic acid (7-ACA) in an aqueous acetone medium, with the corresponding thiol under reflux with pH held to 7.4–7.8. Nannini et al (Arzneim.-Forsch./Drug Res., 27 (I), 2, 343, 1977) also describe similar reactions, but they do not describe the yields and characteristics of the products described therein. With these and other methods, the reaction mixtures of 7-ACA and thiols give compounds having an earthy appearance and a dark brown colour. The high content of various impurities and their difficult elimination cause great losses, with a reduction of the yield. Therefore, the isolated raw products are usually used without subsequent treatment, in the preparation of the N-acyl derivatives, as mentioned in publications and patents. The purification is effected on the end product, with a greater level of loss, as the present inventors have observed.

The experts in the art know that the processes for the preparation of 3-substituted 7-aminocephalosporanic acids are plagued by numerous drawbacks:
(1) loss of carbon dioxide by decarboxylation in the 4 position of the 7-aminocephalosporanic acid
(2) reaction between two equivalents of 7-aminocephalosporanic acid
(3) decomposition of the heterobicyclic system, by intramolecular reaction
(4) formation of by-products with chromophores having a powerful absorption in the visible spectrum region
(5) lactonisation process
(6) decomposition of the 3-substituted 7-aminocephalosporanic acid resulting from the main reaction
(7) difficulties in purifying the substitution product
(8) formation of substantial amounts of mixed 7-aminocephalosporanic and 7-aminopolycephalosporanic acids, responsible for toxicity and allergies, caused by the cephalosporins resulting from the subsequent acylation reaction (9) formation of products having a resiny appearance

(10) technological complexity, particularly with the N-acyl derivatives, as a starting product, for the substitution and subsequent elimination of the acyl group side chain in C-7.

SUMMARY OF THE INVENTION

In view of all the foregoing, the inventors have carried out research with a view to the preparation of a simple method capable of exploitation on an industrial scale and free from the above drawbacks for the substitution of the acetoxy group of 7-ACA and the like, with a high yield and purity.

As a result of the research, it has been found, surprisingly, that the known substitution reaction may be conducted at pH 4.2–5.9, against the theoretical predictions, according to which the nucleophily of the nucleophilic reactant loses a large part of its activity under such conditions. Also, the 7-ACA is close to the isoelectric pH which characterises its maximum degree of insolubility and, therefore, the reaction should not be possible.

The object of the present invention is to provide a process for the production of a 3-substituted 7-aminocephalosporanic acid, of interest as an intermediate for the preparation of cephalosporins, obtainable with a high yield and purity from a 7-aminocephalosporanic acid using simple technology. Further objects and advantages of the invention will be evident from the following description.

In accordance with the invention there are prepared 3-substituted 7-aminocephalosporanic acids of the following general formula I:

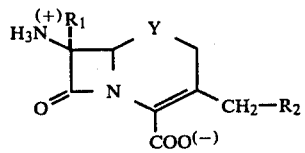

(I)

where Y is oxygen, nitrogen or sulphur or a sulphoxide group $R_1$ is hydrogen or a $C_1$-$C_4$ alkoxy group, preferably methoxy, or a lower alkyl group such as methyl, and $R_2$ is a group selected from among azido ($N_3^-$) or a group having the following formula II: where $R_3$ may be an aromatic, alkanoaromatic, heterocyclic or heterobicyclic nucleus, the process consisting of reacting a cephalosporanic acid represented by the general formula III:

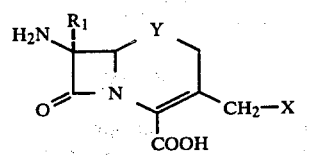

(III)

where $R_1$ and Y are as hereinbefore defined and X is a halogen, acyloxy or carbamoyloxy group, preferably the acetoxy group, with sodium azide or a compound of the formula $R_3$—SH (where $R_3$ is as defined in formula II), such as thiol or mercapto derivative. When Y is a sulphoxide group, with the presence of a reducer in the reaction medium, said group becomes a sulphur atom.

In the general formula II, $R_3$ is a thiol residue known in the field of cephalosporins, and includes, for example, substituted or unsubstituted alkyl, cycloalkyl, aralkyl, acyl, thiocarbamoyl, alkoxythiocarbonyl, aryloxythiocarbonyl and heterocyclic mercapto derivatives. More specifically, they may be methyl, butyl, phenyl, benzyl, furyl, thienyl, oxazolyl, thioxazolyl, thiadiazolyl, triazolyl, tetrazolyl, benzoxazolyl, imidazolyl, pirazolyl, pyridyl, pirazinyl, pyrimidinyl, quinazoline, quinoline, triatriazolyl, benzimidazolyl, purinyl, pyridine-1-oxido-2-yl, pyridazine-1-oxido-6-yl, tetrazolylpyridizanilyl and the like. As heterocyclic groups for $R_3$, the nitrogenated groups containing at least one atom of nitrogen with or without an atom of oxygen and sulphur are preferable.

Moreover, the $R_3$ groups may be substituted by at least one halogen, $C_1$-$C_4$ alkyl, phenyl, hydroxyl, amino, acetamido, nitro, cyano, acyloxy, carboxyl, N,N-dialkyl, $C_1$-$C_4$ sulphoalkyl, alkoxy such as methoxy, sulphamoyl, $C_1$-$C_4$ alkyl carbamoyl. Among these substituents, the hydroxyl, mercapto, amino and carboxyl groups may be blocked with a suitable protector group, of the type habitually used in the field of penicillins and cephalosporins.

The process of the invention consists of reacting 7-aminocephalosporanic acid in an aqueous medium with a mercapto compound, as expressed in scheme I, where X, Y, $R_1$ and $R_3$ are as hereinbefore defined, at temperatures lying between 30° and 95° C., at a reaction isoelectric pH lying between 4.2 and 5.9.

SCHEME I

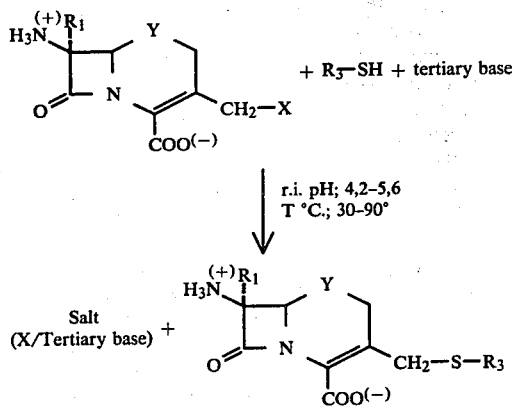

Isoelectric pH values of several 7-aminocephalosporanic acids, at saturation in water and at different temperatures, are given in Table 1. This pH characterises the maximum insolubility of the compound and its maximum stability to the effect of heat. Likewise, under these pH and temperature conditions, the reactants are isolated practically unaltered after 60 min at, for example, 80° C., namely, the 7-aminocephalosporanic acid and the thiol compound.

It has now been discovered that the conversion of a 7-amino-3-acetoxymethyl-3-cephem-4-carboxylic acid into another 3-substituted 7-aminocephalosporanic acid may be conducted at pH ranges close to the isoelectric pH. This pH range is known as reaction isoelectric pH at a particular temperature.

It is characterised by:

1. The notable evolution of the pH during the reaction.

2. The product resulting from the substitution precipitates.
3. An optimum conversion temperature.

At the reaction isoelectric pH (r.i.pH), the aqueous medium is constituted by an aggregate of ionic species of the 7-aminocephalosporanic acid, precursor of the zwitterion. During the displacement, an acetate ion and a new aggregate is formed, the latter evolves preferably to the zwitterion and precipitates out. Both effects become sensitive to the pH measurements. The equilibrium between the zwitterion and the ionic species aggregate is also affected by the concentration. In accordance with this, the evolution of the initial system, at limit dilutions, for example 4%, in the starting 7-aminocephalosporanic acid, the r.i.pH values also undergo a change, reaching the range of 5.80–5.90 and the reaction product may remain in solution at the reaction temperature. The precipitation may also occur at a very advanced stage of the conversion, which situation is reflected in Example 3.

7-aminocephalosporanic acid, for one volume of aqueous solution, at the desired temperature. The proportions of the different components of the mixture are determined by pH measurements. The pH values of aqueous thiol solutions are also orientative and some are given in Table 2. With the tertiary amine pH data given in the literature it is easy to forecast and, moreover, determine experimentally, the pH of solutions formed by a thiol and the tertiary base. The subsequent incorporation of the 7-aminocephalosporanic acid provides the desired pH adjustment.

TABLE 2 pH of thiol compounds in aqueous solutions.

| THIOL | [%] p/v | T °C. 60 | T °C. 70 | INITIALS (x) |
|---|---|---|---|---|
| THIOACETIC ACID | 1,00 | 2,36 | 2,40 | TA |
| 1-METHYL-5-MERCAPTOTETRAZOLE | 1,00 | 2,63 | 2,72 | MTA |
|  | 2,00 | 2,56 | 2,64 |  |
| 1-PHENYL-5- | 0,35 | 2,59 | — | PhT |

TABLE I

| INITIALS | $R_2$ ($R_1$ = H) | Isoelectric pH of I. Saturation at different temperatures (0.1%) | | | | | |
|---|---|---|---|---|---|---|---|
| | | 22° C. | 30° C. | 40° C. | 50° C. | 60° C. | 70° C. |
| (7-ACA) | $CH_3COO^-$ | 3,85 | 3,80 | 3,74 | 3,67 | 3,60 | 3,54 |
| (7-ACA—$N_3$) | $N_3-$ | 4,11 | 4,05 | 3,98 | 3,90 | 3,81 | 3,73 |
| (MTA) | N-methyltetrazole-thio | 4,25 | 4,20 | 4,11 | 4,02 | 3,95 | 3,80 |
| (TA) | $CH_3COS-$ | — | 4,13 | 4,08 | 4,02 | 3,94 | 3,86 |
| (TD) | methylthiadiazole-thio | 4,21 | 4,19 | 4,12 | 4,05 | 3,97 | 3,90 |
| (PhT) | phenyltetrazole-thio | 4,69 | 4,68 | 4,62 | 4,55 | 4,46 | 4,32 |
| (AT) | amino-thiadiazole-thio | 4,35 | 4,32 | 4,25 | 4,18 | 4,11 | 4,04 |
| (MT) | thiazoline-thio | 4,38 | 4,31 | 4,21 | 4,06 | 3,84 | 3,65 |

From the adjusted saturation isoelectric pH values for certain 7-aminocephalosporanic acids given in Table I, it was not possible to foresee the sensitivity and behaviour of the products at r.i. pH. These results constitute the object of this invention and may be considered to be surprising.

For the purpose of the invention, there are selected preferably r.i. pH values lying between 4.2 and 5.6, at reaction temperatures lying between 30° and 95° C. Such r.i. pH values are attained by the combination of a proportion of a thiol compound, a tertiary base and the

| | | | | |
|---|---|---|---|---|
| MERCAPTOTETRAZOLE | 0,50 | — | 2,50 | |
| 5-METHYL-2-MERCAPTO-1,3,4-THIADIAZOLE | 0,90 | 3,60 | — | TD |
| | 1,20 | 3,08 | — | |
| | 1,42 | — | 3,00 | |
| 2-AMINO-5-MERCAPTO-1,3,4-THIADIAZOLE | 0,72 | 3,87 | — | AT |
| | 1,03 | — | 3,77 | |
| 2-MERCAPTO-1,3-THIAZOLINE | 3,50 | 4,39 | 4,40 | MT |
| THIOPHENOL | Saturation 4,37 (23° C.) | — | | TPh |

(x) Abbreviations used in the specification.

Essentially there is determined an r.i. pH close to the isoelectric pH of the desired 3-substituted 7-aminocephalosporanic acid such that the reaction should cause precipitation. For the isolation of any fraction that remains in solution, the mixture pH is adjusted to room temperature to 4.0 to 5.0. This pH is properly the isolation pH and its range may coincide with some r.i. pH value.

The temperature may be set to between 30° and 95° C. and the times may range from 30 to 180 minutes. Preferably, relatively short times and temperatures ranging from 40° to 70° are chosen.

The chemical process for the conversion of the acetoxy group, starting out from 7-aminocephalosporanic acid (known as 7-ACA) or from 7-amino-7-methoxycephalosporanic acid (known as 7-AMCA) or 7-amino-7-methylcephalosporanic acid (known as 7-AMECA) with a mercapto compound in an aqueous medium for the formation of the product of formula I is effected, according to the invention, for example, as shown specifically in Scheme 2, for the substitution with 2-mercapto-5-methyl-1,3,4-thiadiazole to obtain the corresponding derivative, known as 7-ACA-TD.

the experts. Thus, for example, in the case of Example 4, conducted according to Scheme of the Figure, apart from achieving a yield of 95% of the theoretical value, the purity by evaluation of the amino and carboxyl groups is 99/100%. The purity checked by ultraviolet spectroscopy in the visible range at 450 nm of a 1% 7-ACA-TD solution in aqueous triethylamine solution (2% v/v triethylamine/water) gives absorbance values lying between 0.100 and 0.250, whereas for an analytical sample $A_{450}=0.050$ (e=1 cm).

For the object of the present invention, a general formula for carrying out the process consists of the preparation of a solution comprising the water, the mercapto derivative and its organic tertiary base salt. Thereafter a set weight of 7-ACA or 7-AMCA or 7-AMECA is added to obtain a concentration preferably of from 0.4 to 4% at the reaction isoelectric pH. For the treatment, the prior addition of boric acid, or the introduction of a current of carbon dioxide, trimethylacetic acid, 2-ethylhexanoic acid and the like are auxiliary components for adjusting the pH to the 7-aminocephalosporanic acid concentration, which may even be up to 8%.

SCHEME 2

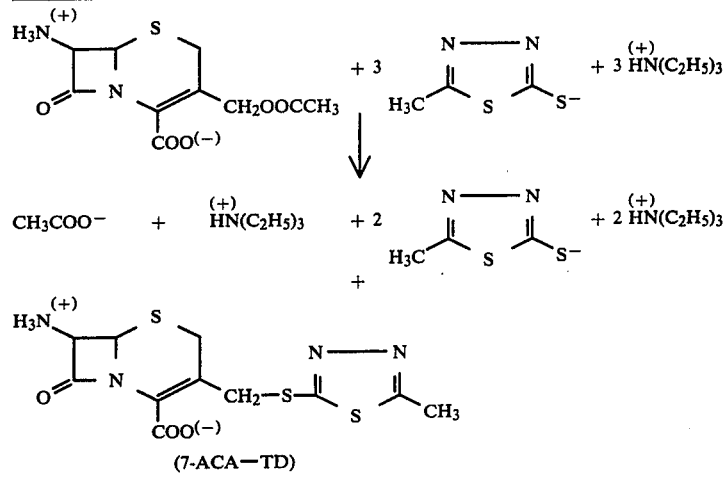

Although a stoichiometric ratio of 1:3 is cited in Scheme 2, for the 7-ACA/mercapto-triethylamine salt, it may comprise other values, e.g. 1:1.5 for a 1.33% reaction mixture volume of 7-ACA to obtain the r.i. pH.

The analytical profile of the reaction isoelectric pH allows for alternative technologies to be used, as shown in the Figure.

The reaction mixture volume, the temperature thereof and optimum pH, for example, between 4.2 and 4.9, are chosen to attain the formation of a solution, with the amounts expressed in Example 4. After 15 minutes reaction time in a reactor A, the mixture is caused to flow continuously through the solid-liquid B separator, where the 7-ACA-TD, which precipitates out, is retained. In this way, the process is controlled and the 7-ACA-TD is isolated from the solution components and from an extended thermal effect. The flow is facilitated by the pump F and a vacuum gradient (E) between A and C. The temperature is held constant through the preheater D and the steam condensation is controlled with the heat exchanger G.

The advantages provided by the continuous preparation and isolation method, such as optimization of the yield, purity and simple technology will be evident to The mercapto compound salts, included in the general formula $R_3$—SH, adequate for the end purpose of the process, are prepared in the aqueous medium with the mercapto compound and the chosen tertiary base. These may be selected from among the group of the bicyclic amidines, such as DBN and DBU, respectively, 1,5-diazabicyclo[4.3.0]non-ene and 1,5-diazabicyclo[5.4.0]undec-5-ene, and the like, heterocyclic bases such as pyridine, picolines, lutidines and quinoleins, tertiary amines such as tributylamine, tripropylamine and the like. The proportion of these salts may vary relative to the stoichiometry, up to four times more. The excess may then be recovered from the mother liquors resulting from the reaction and also from the liquors used for washing the 3-substituted 7-aminocephalosporanic acid isolated from the mixture. All those amines are also conveniently used to form combinations to obtain the reaction isoelectric pH.

In the case of substitution by means of sodium azide, Example 1, since the salt is basic, the reaction isoelectric pH is adjusted to pH 5.9, by addition of the appropriate amount of trimethylacetic acid. Under the dilution conditions for the reaction, the 7-amino-3′-azidocephalosporanic acid is precipitated at the isolation pH of 4.3 (5° C.). If the corresponding DBU salt (azide-DBU) is used, the r.i. pH is adjusted to between 5.2–5.5.

Within the purposes of the invention, the reaction mixture at the r.i. pH need not be a solution initially, it may be constituted by a partial suspension of one of the components. Nevertheless, it is preferable to conduct the conversion, obtaining initially a complete solution and the chemical process is characterised by the following physico-chemical parameters:

A. Temperature
  1. Preparation temperature of the aqueous 7-aminocephalosporanic acid solution or of its isosteres.
  2. Temperature of the reaction isoelectric pH range.
  3. Isolation temperature
B. Analytical profile of the process pH
  1. pH of the thiol and tertiary base mixture.
  2. pH of the solution formed with the 7-aminocephalosporanic acid or its isosteres.
  3. Reaction isoelectric pH.
  4. Isolation pH.
C. Reaction isoelectric pH regulators
  1. Carbon dioxide and weak tertiary amine salts.
  2. Weak inorganic acids, such as boric acid.
  3. Weak organic acids, such as trimethylacetic, isononanoic, 2-ethylhexanoic and similar acids.
  4. Aminoacids having an isoelectric pH of the order of the 7-aminocephalosporanic acids or their isosteres.
  5. Mercapto compounds.
D. TIME. From 30 to 180 minutes, according to the reaction temperature.

One practical way of operating is characterised in that the reaction temperature need not be the solution temperature. To this end, the reaction mixture containing a 7-aminocephalosporanic acid or an isostere to be substituted, is heated to the temperature at which solution takes place, for example between 75° and 95° C. Thereafter the resulting solution is cooled in a short time to the reaction temperature, for example, selected between 40° and 60° C. This temperature is preferably adopted, in accordance with the r.i. pH causing precipitation of the 3-substituted 7-aminocephalosporanic acid. Finally, the isolation temperature may coincide with the reaction temperature, such as room temperature or close thereto. The remainder of the product formed is isolated from the mother liquors, adjusted to the isolation pH.

A further alternative of the method consists of preparing the 7-aminocephalosporanic acid solution at one temperature, then adding the acid component until the r.i. pH is reached and then cooling to the reaction temperature which is lower than the solution temperature.

When using very water-insoluble thiol compounds, a convenient proportion of a miscible organic solvent, such as the lower alcohols, acetone, ethylene glycol and 1,2-dimethoxyethane may be added to the reaction medium. The amount of the latter is adjusted according to the solubility of the thiol in the mixtures with water at the r.i. pH. Thus, in the case of thiophenol, Example 12, the absence of isopropanol causes precipitation of the product in form of a paste; an excess of alcohol causes a drop in yield. The use of 1,2-dimethoxyethane, on the other hand, increases the yield. The importance of the r.i. pH is also reflected in Example 1, at which pH, the 7-ACA-N₃ remains in solution at the reaction temperature. Its r.i. pH, around 4.6, at which precipitation takes place, shows that the conversion must be continued at 50° C., controlling the pH with shorter reaction times. Thus an increase in yield is obtained, particularly, with the salt of hydronitric acid and a bicyclic amidine.

Now, with the results of isoelectric pH measurements given in Tables 1 and 2, it is possible to determine the optimum conditions of the chemical process to obtain a high yield and purity for each specific case of the displacement reaction. From an examination of those data, Tables 1 and 2, it is deduced that the reaction evolves from one isoelectric pH of the 7-amino-3-acetoxymethyl-3-cephem-4-carboxylic acid to a higher isoelectric pH, given by the product resulting from the substitution. This pH range constitutes the reaction isoelectric pH (r.i. pH) providing the most favourable conditions for the process. This may comprise, as possible starting products, the 7-aminocephalosporanic acids and their isosteres, the 7-aminooxacephalosporanic acids and 7-aminoazacephalosporanic acids, all know.

For the preparation of the process of elimination of the acetoxy group, for each particular case and at a particular r.i. pH range, the parameters are controlled first by infrared spectroscopy and then the corresponding process parameters are adjusted, according to the results of the proton magnetic resonance. All the compounds prepared in this way may be used directly for the acylation reactions; nevertheless, if wished, they may be purified by simple solution in hydrochloric acid, decolouring with activated carbon and precipitation at pH 1.8–2.2 (20° C.), with a high yield and virtually analytical purity.

To facilitate the understanding of the foregoing ideas, there are described hereinafter certain examples of the invention, which, in view of their merely illustrative nature, must be deemed to be lacking in any restrictive effect on the scope of legal protection being applied for.

EXAMPLE 1

7-amino-3(azidomethyl)-3-cephem-4-carboxilyc acid (7-ACA-N₃)

82.5 g of triethylamine hydrochloride were added to a solution of 40 g of sodium azide in three liters of water. Thereafter there were added 30 g of 7-aminocephalosporanic acid (90%), causing a change of pH from 7.15 (20° C.) to 5.24 at 50° C. The mixture was stirred for 60 min at 70° C., the pH progressing from 5.1 to 5.6. 6 g of activated carbon were added over the last 30 min, in three portions, one every ten minutes. The mixture was filtered and adjusted to pH 4.60 at 40° C., with the addition of acetic acid, the precipitation being initiated. The mixture was cooled to 5° C. and the pH readjusted to 4.24. After 30 min, the solid, after being filtered, washed with water and acetone, gave 14.0 g of the compound of the title, with a 54% yield. Decomposes at 225° C.

$C_8H_9N_5O_3S$ Calculated: C, 37,64; H, 3,55; N, 27,44; S, 12,56; (255,24). Found: C, 37,50; H, 3,51; N, 27,36; S, 12,50.

IR(KBr) $\nu$: 2100 (N₃, intense) 1802 (C=O beta-lactam), 1620 (carboxylate) and 1535 (NH₃⁺, broad band) cm⁻¹.

¹H—NMR(F₃CCOOH) δ ppm: 3,34 (2H,s,H-2); 4,5 (2H,c,CH₂N₃; J=15.0 Hz); 5,03 (2H,s,H-6,H-7).

EXAMPLE 2

7-amino-3[(5-methyl-1,3,4-thiadiazol-2-yl)thiomethyl]-3-cephem-4-carboxylic acid (7-ACA-TD)

A suspension of 40 g (0.30 mole) of 2-mercapto-5-methyl-1,3,4-thiadiazole (TD) in 3.15 liters of water, with 30 g of boric acid and 30.4 ml ($\simeq$0.217 mole) of triethylamine was heated to 70/72° C. While the mixture was being vigorously stirred, at the same temperature, one 40 g shot (0.147 mole) of 7-amino-3-acetoxymethyl-3-cephem-4-carboxylic acid (92%) was added.

The resulting solution, with a reaction isoelectric pH of 4.98, dropped to 4.92 (71°-72° C.) and was stirred for 60 min. The precipitation started after 6 to 8 min and the isoelectric pH evolved to a value of 5.3. Thereafter it was cooled to 50° C. and the pH was adjusted to 4.8 with 1N hydrochloric acid ($\simeq$15.2 ml in all) and was finally readjusted at 20° C. After cooling to 5°-10° C. for 15 min, the solid was isolated by filtration, washed successively with water and acetone and after drying at 40° C., it gave 46.0 g of the compound of the title, with a 97% yield, 96% purity (determined by the usual methods) and a melting point of 225° C. with decomposition.

IR (KBr)$\nu$: 1802 (beta-lactam), 1618 (carboxylate), 1543 ($NH_3^+$, broad) $cm^{-1}$.

$^1$H-NMR ($F_3CCOOH$)$\delta$ ppm: 2,76 (3H,s,$CH_3$); 3,50 (2H,s,H-2); 4,37 (2H,c,$CH_2S$; J=15,0 Hz); 5,05 (2H,s, H-6, H-7).

EXAMPLE 3

7-ACA-TD

When the amounts of Example 2 were used and the boric acid was replaced by a carbon dioxide flow in a volume of 9 liters of water for the reaction mixture, the reaction isoelectric pH was about 5.0. Precipitation started about 40 min after start of treatment. On cooling, the precipitate increased and the pH was adjusted to 4.8 at 20° C. After 20 min the solid was isolated as described in Example 2 to give 38.85 g of the compound of the title, with identical properties.

EXAMPLE 4

Continuous separation process for 3-substituted 7-aminocephalosporanic acids I. The reactor A was charged with:
1—3,000 liters of deionised water.
2—60 kg of a compound selected from among TD, PhT, AT, MT, TPh or an equivalent amount of a thiol compound selected from among the products defined at the end of the Example, in V.
3—30/45 liters of a tertiary base, e.g. triethylamine, adjusted to the amount of the product selected in 2.
4—The mixture was heated with stirring to a temperature selected between 55° and 75° C.

II. At the chosen temperature, reactor A was charged with:
1—60 kg of a compound selected from among 7-ACA, 7-AMCA or 7-AMECA, incorporated in one shot.
2—The reaction isoelectric pH, of from 4.2 to 5.9, was obtained in the resulting solution, in accordance with the amounts of the components of the mixture.
3—The control of the reaction isoelectric pH may be supplemented by the addition of boric acid or, as the case may be, by a proportion of the thiol compound or by adding trimethylacetic acid or a weak tertiary base acetate to the mixture or with a current of carbon dioxide.

III. After stirring the mixture for 10 to 15 min and heating to the specifically selected temperature, it is pumped through the solid/liquid separator B by pump F, is recirculated through the preheater D. The operative time was between 60 and 240 min.
1—After approximately 50% of the reaction time, between 55% and 75% of the total conversion product had been retained in the separator B.
2—From this time onwards, there was metered in C an amount of a suspension of carbon in water such as to give a final carbon content in the reaction mixture of from 0.5 to 1%. The circulating liquors were shunted towards the carbon retaining filter.
3—The absorbancy of the solution was checked by testing a sample in an ultraviolet spectrometer in the visible region at about 450 nm.

IV. After all the starting 7-aminocephalosporanic acid had been processed, isolation was initiated:
1—The liquors were retained in the reactor A and cooled. The pH was adjusted to from 3.5 to 4.8 by addition of an amount of a conventional acid.
2—The pH was readjusted at 20° C. and after a period of time (30 min) the liquors were racked through the separator B.
3—The solid was washed successively with water and acetone. The acetone liquors were put aside for recovery of the excess thiol derivative.
4—The isolated product was dried at 40° C. by the usual processes.

The result was an amount of 3-substituted 7-aminocephalosporanic acid with a yield of from 70% to 95%, depending on the nature of the thiol and in general conforming to the Examples which are specifically described in the invention.

V. According to the process, the following compounds are obtained with similar yields:

7-amino-3-[2-(1,3,4-thiadiazolyl)thiomethyl]-Δ3-cephem-4-carboxylic acid.

7-amino-3-[5-(1-sulphomethyl-1,2,3,4-tetrazolyl)thiomethyl]-Δ3-cephem-4-carboxylic acid.

7-amino-3-[2-(5-metyl-1,3-oxazolyl)thiomethyl]-Δ3-cephem-4-carboxylic acid.

7-amino-3-[2-(1-methyl-1,3,4-triazolyl)thiomethyl]-Δ3-cephem-4-carboxylic acid.

7-amino-3-[2-(5-phenyl-1,3,4-thiadiazolyl)thiomethyl]-Δ3-cephem-4-carboxylic acid.

7-amino-3-[5-(1,2,3,4-tiatriazolyl)thiomethyl]-Δ3-cephem-4-carboxylic acid.

7-amino-3-[2-(5-methyl-1,3,4-triazolyl)thiomethyl]-Δ3-cephem-4-carboxylic acid.

7-amino-3-[2-(imidazolyl)thiomethyl]-Δ3-cephem-4-carboxylic acid.

7-amino-3-[2-(5-ethoxicarbonylmethyl-1,3,4-triazolyl)-thiomethyl]-Δ3-cephem-4-carboxylic acid.

7-amino-3-[5-[2-(2-carbamoyl)ethyl-1,2,3,4-tetrazolyl]-thiomethyl]-Δ3-cephem-4-carboxylic acid.

7-amino-3-[5-[1-(2-sulphamoyl)ethyl-1,2,3,4-tetrazolyl]-thiomethyl]-Δ3-cephem-4-carboxylic acid.

7β-amino-7α-methoxi-3-[2-(5-methyl-1,3,4-thiadiazolyl)thiomethyl]-Δ3-cephem-4-carboxylic acid.

7-amino-3-[5-[2-(2-dimethylaminoethyl)-1,2,3,4-tetrazolyl]thiomethyl]-Δ3-cephem-4-carboxylic acid.

7-amino-3-[2-(benzoxazolyl)thiomethyl]-Δ3-cephem-4-carboxylic acid.

7-amino-3-o5-(1,2,3-triazolyl)thiomethyl]-Δ3-cephem-4-carboxylic acid.

7-amino-3-propilthiomethyl-Δ3-cephem-4-carboxylic acid.

7-amino-3-(ethoxycarbonylmethylthiomethyl)-Δ3-cephem-4-carboxylic acid.

EXAMPLE 5

7-amino-3[(1,3-thiazolin-2-yl)thiomethyl]-3-cephem-4-carboxylic acid (7-ACA-MT)

A suspension of 105 g (≃0.79 mole) of 2-mercapto-1,3-thiazoline (MT) in 3 liters of deionised water and 32 ml (0.22 mole) of triethylamine was heated with vigorous stirring to 60°–62° C. At this temperature there was added in one shot 60 g (0.22 mole) of 7-amino-3-acetoxymethylcephalosporanic acid (88% purity). Over a period of 90 min the reaction isoelectric pH had evolved from 5.2 to 5.5. The precipitation started after the first 7 to 10 min after the onset of treatment and increased with the reaction time. Thereafter the mixture was cooled to 40° C. and the pH was adjusted to 4.17 with 1N hydrochloric acid (≃16.4 ml) and was adjusted to 4.10 at 20° C. The separated solid was filtered, washed successively with water and acetone and after drying at 40° C., it gave 52.0 g of the compound of the title with an 80% yield. The solid was resuspended in 650 ml of dichloromethane, 15 ml of beta-picoline was added and after 30 min stirring at room temperature, the solid was recovered by filtration, washed with acetone and dried. Decomposes without melting at 185°–190° C.

$C_{11}H_{13}N_3O_3S_3$. Calculated: C, 39,86; H, 3,95; N, 12,68; S, 29,02; (331,42). Found: C, 39,60; H, 4,00; N, 12,65; S, 28,85.

IR(KBr)ν: 1802 (C=O, beta-lactam), 1615 (carboxylate) and 1550 ($NH_3^+$, broad band with two sub-bands) cm$^{-1}$.

$^1$H-NMR($F_3$C-COOH+$D_2$O)δ ppm: 3,45(2H,s,H-2); 3,60-4,70(6H, complex, $CH_2S,CH_2N$); 5,00(2H,s,H-6,H-7).

EXAMPLE 6

7-amino-3-[(1-methyl-1,2,3,4-tetrazol-5-yl)thiomethyl]-3-cephem-4-carboxylic acid (7-ACA-MTA)

A solution of 72.5 g of 1-methyl-5-mercapto-1,2,3,4-tetrazole (MTA) in 87.5 ml of triethylamine in 3 liters of water was heated to 75° C. 68 g of 7-aminocephalosporanic acid (92%) were added, to give a suspension with pH 4.35. 28 ml of triethylamine were added at the same temperature and the solution thus formed, with pH 5.20, was held for 30 min at 75° C. and 60 min at 53° C. Throughout the whole operation the reaction isoelectric pH was held to 5.25 with the gradual addition of a solution of 20 g of thiol (MTA) in 175 ml of water. The formation rate of the precipitate increased on cooling to 53° C. The mixture was adjusted to pH 4.25 at 25° C. with concentrated hydrochloric acid. It was filtered, washed with water and then acetone to give 52.8 g of the compound of the title with a 70% yield. It was recrystallised out of an aqueous hydrochloric acid solution at pH 2.20 and isolated with a m.p. 224° C. (d).

$C_{10}H_{12}N_6O_3S_2$. Calculated: C,36,58; H,3,68; N,25,59; S,19,52; (328,35). Found: C,36,0; H,3,7; N,25,3; S,19,2.

IR(KBr)ν: 1800(beta-lactam), 1618(carboxylate), 1540($NH_3^+$, broad band).

$^1$H-NMR($F_3$CCOOH) δ ppm: 3,49(2H,s,H-2); 3.79(3H,s,$NCH_3$); 4,16(2H, C partial overlap, $CH_2S$; J=15,0 Hz) 5,03(2H,s,H-6,H-7).

EXAMPLE 7

7-ACA-TD: Combination of bases

A solution of 118.8 g of 2-mercapto-5-methyl-1,3,4-thiadiazole (TD), 62.4 ml of DBN and 38 ml of beta-picoline in 3 liters of water was heated to 70° C., there was added in one shot 109 g of 7-amino-3-acetoxymethyl-cephalosporanic acid (7-ACA; 90%). The mixture was stirred vigorously for 60 min at 69°–70° C. and then for 30 min at 60° C. Thereafter it was cooled to 20° C. and 712 ml of 1N hydrochloric acid were added. The solid was filtered and washed successively with water and acetone to give 108 g of the compound of the title. It was slightly coloured, but this may be avoided by continuous separation as precipitation proceeds, as from 15 minutes after the onset of the reaction.

Analytical profile of the process pH at 69°–70° C.:
1—TD suspension; pH=2.8–2.9.
2—Addition of DBN; pH=5.51.
3—Addition of beta-picoline; pH=5.70.
4—Solution with 7-ACA; pH=5.30
5—Reaction isoelectric pH: evolution from 5.28 to 5.42.
6—Isolation pH: 4.2 at 20° C.

The compound had similar properties to the one prepared in the previous Examples.

EXAMPLE 8

7-amino-3-(1-phenyl-1,2,3,4-tetrazo-5-yl)thiomethyl-3-cephem-4-carboxylic acid (7-ACA-PhT)

A suspension of 53.4 g (0.3 mole) of 1-phenyl-5-mercapto-1,2,3,4-tetrazole (PhT) in 4 liters of water was heated to 70° C. with vigorous stirring and 42 ml of triethylamine (0.3 mole) were added thereto. 40.8 g of 7-amino-3-acetoxymethyl-cephalosporanic acid (7-ACA, 90/92%) were added to the resulting colourless solution in one shot. The suspension was stirred for 100 minutes. Thereafter it was filtered while hot to isolate the solid which was washed with water and acetone. The mother liquors were decoloured and adjusted to pH 4.2, to give a further portion of 1.4 to 1.8 g.

The analytical profile of the process pH at 69°–70° C. was:
1—PhT suspension; pH≃2.35.
2—Solution containing triethylamine; pH≃4.50.
3—Suspension of 7-ACA; pH≃4.10–4.20.
4—Reaction isoelectric pH; evolved from 4.20 to 5.60.
5—Isolation pH; 5.60.

In all, 49.5 g of the compound of the title were obtained, with a 94% yield, a slightly straw coloured, white product, m.p. 222°–225° C. with decomposition (analytical sample: m.p. 225°–227° C. with decomposition).

$C_{15}H_{14}N_6O_3S_2$. Calculated: C,46,14; H,3,61; N,21,52; S,16,42; (390,43). Found: C,46,00; H,3,60; N,21,50; S,16,35.

IR(KBr)ν: 1800(C=O, beta-lactam); 1618(carboxylate) and 1520 ($NH_3^+$, broad band with readings at 1538 and 1498) cm$^{-1}$.

$^1$HNMR($F_3$CCOOH) δ ppm: 3,48(2H,s,H-2); 4,37(2H,s,$CH_2S$); 4,98 (2H,s,H-6,H-7); 7,25(5H,s,arom.).

EXAMPLE 9

7-ACA-PhT: Process with 1.5-diazabicyclo [5.4.0]undec-5-ene (DBU)

Example 8 was followed, but the triethylamine was replaced by an equivalent amount of DBU. The reaction isoelectric pH values were of the same order and the compound of the title was obtained with a similar yield.

EXAMPLE 10

7-amino-3-[(2-amino-1,3,4-thiadiazol-5-yl) thiomethyl]-3-cephem-4-carboxylic acid (7-ACA-AT)

A suspension of 106.4 g (0.8 mole) of 2-amino-5-mercapto-1,3,4-thiadiazole (AT) in 4.8 liters of water was heated to 70° C. 56.0 ml of triethylamine (0.4 mole) were added and after 5 minutes stirring, 54.4 g (0.2 mole) of 7-amino-3-acetoxymethyl-cephalosporanic acid (7-ACA; 92–93%) were added in one shot. After 15 minutes vigorous stirring, an abundant precipitation had already been formed. After 40 minutes, the mixture was adjusted to pH 4.24 with approximately 342 ml of 1N hydrochloric acid and the solid was isolated by filtration at 20° C. It was washed successively with water, methanol and acetone. 67.6 g were obtained with a 98% yield and m.p. 218°–222° C.

The analytical profile of the process pH at 69°–70° C. was:
1—AT suspension; pH=3.67.
2—Solution containing triethylamine; pH=5.95.
3—Solution with 7-ACA; pH=5.52.
4—Reaction isoelectric pH; evolved from 5.52 to 5.60.
5—Isolation pH; 4.24 at 20° C.

The excess AT was recovered from the methanol liquors.

IR(KBr)$\nu$: 330(NH$_2$); 3120(thiadiazole); 1800(beta-lactam); 1620(band with two peaks at 1635 and 1618); 1520 (NH$_3^+$, broad band between 1540 and 1500) cm$^{-1}$.

$^1$H-NMR(F$_3$CCOOH+D$_2$O) $\delta$ ppm: 3,51(2H,s,H-2); 4,23 (2H,c,CH$_2$S; J=15,0 Hz); 5,05(2H,s,H-6,H-7).

EXAMPLE 11

7$\beta$-amino-7$\alpha$-methoxy-3-(1-methyl-1,2,3,4-tetrazol-5-yl)-thiomethyl-3-cephem-4-carboxylic acid (7-AMCA-MTA)

A solution of 3.14 g (0.03 mole) of 1-methyl-5-mercapto-1H-tetrazole (MTA) in 300 ml of water and 4.2 ml (0.03 mole) of triethylamine was heated to 60° C. 2.48 g (0.0075 mole) of 7$\beta$-amino-7$\alpha$-methoxy(3-acetoxymethyl)-3-cephem-4-carboxylic acid (7-AMCA) were added in one shot. The mixture was vigorously stirred for 100 minutes. Carbon dioxide was blown through throughout the whole operation and the reaction isoelectric pH evolved from 4.9 to 5.3. The mixture was then cooled to 20° C. and adjusted to pH 4.18. The solid was filtered, washed with water and acetone to give the compound of the title.

A portion of 7-AMCA-MTA, with 4-hydroxy-3,5-di-t-butylbenzaldehyde in methanol and dicyclohexylamine gave the corresponding benzylidene derivative by evaporation of the solvent.

$^1$N-NMR(CDCl$_3$) $\delta$ ppm: 1,35(18H,s,C (CH$_3$)$_3$; 3,48(3H,s,OCH$_3$), 3,80(3H,s,NCH$_3$); 4,42(2H,s,Cl-H$_2$); 4,98(1H,s,C6-H); 5,60(OH); 7,61(2H,s, aromatic); 8,47(1H,s,CH=N).

EXAMPLE 12

7-amino-3(phenyl-thiomethyl)-3-cephem-4-carboxylic acid (7-ACA-TPh)

First 61.8 ml of thiophenol (0.6 mole) and then 56 ml of triethylamine (0.04 mole) were added to a mixture of 2.5 liters of water and 0,5 liters of isopropanol. It was thereafter heated to 70° C. to give a translucid solution with pH 7.04. Thereafter there were added in one shot 81.6 g of 7-amino-3-acetoxymethylcephalosporanic acid and the mixture was stirred for 30 minutes causing the pH to vary from 6.49 to 5.99 in 10 minutes at 70° C. Under these conditions, the formation of a precipitate was initiated and it increased as the pH varied to 6.18. Stirring was continued for a further 30 minutes at 60° C. and the pH was held to 5.5 by acetic acid. The mixture was adjusted to pH 4.20 with concentrated hydrochloric acid at 20° C. The precipitate was filtered, washed with water and acetone and dried to give 53.0 g of the compound of the title, with a 54.6% yield. The compound was isolated from a p-toluensulphonic acid solution with heating and dilution, with decomposition at 235°–240° C.

C$_{14}$H$_{14}$N$_2$O$_3$S$_2$. Calculated: C,51,99; H,4,36; N,8,66; S,19,83; (323,39). Found: C,51,62; H,4,31; N,8,54; S,19,60.

IR(KBr)$\nu$: 1798(beta-lactam), 1612(carboxylate) and 1540 (NH$_3^+$, broad band) cm$^{-1}$.

$^1$H-NMR(F$_3$CCOOH+D$_2$O) $\delta$ ppm: 3,28(2H,s,H-2); 3,85(2H,c,CH$_2$S; J=13,8 Hz); 4,82(2H,s,H-6,H-7); 7.07(5H,s,arom.).

EXAMPLE 13

7-amino-3[(3-methylisoxazol-5-yl)carbonylthiomethyl]-3-cephem-4-carboxylic acid (7-ACA-ISO)

4.29 g (3 cmole) of 3-methylisoxazole-5-thiocarboxylic acid were dissolved in 300 ml of 60% isopropanol-water and there were added 1.6 ml of DBU (Example 9) and 3 ml of beta-picoline. At 65° C., there were added in one shot 3.0 g of 7-aminocephalosporanic acid, 90%. The mixture was stirred for 90 minutes and the reaction isoelectric pH was held to 5.5. The precipitate which formed was isolated after adjusting the pH to 4.0 at 25° C. by concentrated hydrochloric acid. The precipitate was filtered, washed with water and acetone to give 3.0 g of the compound of the title, with an 80% yield. The infrared and proton magnetic resonance spectra are consistent with its structure.

EXAMPLE 14

7-amino-3-(methylcarbonyl-thiomethyl)-3-cephem-4-carboxylic acid (7-ACA-TA)

56.8 ml (0.8 mole) of thioacetic acid and 140 ml (1.0 mole) of triethylamine were added successively to three liters of water under stirring. The homogenous mixture was heated to 75° C. and there were added in one shot 100.0 g (0.368 mole) of 7-aminocephalosporanic acid (90%), causing a pH variation from 9.05 to 5.03. Thereafter there were added, first, 20 to 21 ml of triethylamine until a solution was formed and then 61.0 g of boric acid. Stirring was continued at 70° C. for 60 minutes and the reaction isoelectric pH was checked, regulating the variation from 5.80 to 5.60 by gradual addition of 10.9 ml of thioacetic acid over a period of about 30 minutes. During the last 15 minutes, the pH varied to a virtually constant value of 5.70. The precipitation increased during the reaction and was completed at 60° C. and the pH was adjusted to 4.80 (25° C.) by the addition of about 300 ml of 1N hydrochloric acid. The solid was filtered, washed successively with water and acetone to give 73.5 g of the compound of the title, with a 77% yield. It turned brown at about 215° C. and decomposed at 228° C. (polarised light). The excess thioacetic acid was recovered from the mother liquors at pH 1.0 by extraction with an organic solvent.

The analytical profile of the process was as follows:
1—Solution temperature: 75° C. (10 minutes)
2—Reaction temperature: 70° C.
3—Reaction time: 60 minutes
4—Solution pH: 5.80–5.90
5—Reaction isoelectric pH: 5.60
6—Isolation pH: 4.80

$C_{10}H_{12}N_2O_4S_2$. Calculated: C,41,66; H,4,19; N,9,71; S,22,24; (228,33). Found: C,41,08; H,4,05; N,9,70; S,21,92.

IR(KBr)$\nu$: 1800(beta-lactam), 1682(acetylthio), 1615 (carboxylate) and 1540($NH_3^+$, broad) cm$^{-1}$.

$^1$H-NMR($F_3$CCOOH) $\delta$ ppm: 2,16(3H,s,$CH_3$CO); 3,34(2H,s,H-2); 4,01(2H,c,$CH_2$S; J=14,4 Hz); 5,07(2H,s,H-6, H-7).

EXAMPLE 15

(7β-amino-7α-methoxy-3-(methylcarbonyl-thiomethyl)-3-cephem-4-carboxylic acid (7-AMCA-TA)

Following Example 14 and replacing the 7-aminocephalosporanic acid with 11.12 g of 7β-amino-7α-methoxy-cephalosporanic acid and the tenth part of the amounts of the remaining components, the compound of the title was isolated with a similar yield. The infrared and proton magnetic resonance spectra are consistent with its structure.

The analytical profile of the process has characteristics substantially identical to those of the previous example.

EXAMPLE 16

7-amino-3-(methoxymethyl-carbonyl-thiomethyl)-3-cephem-4-carboxylic acid (7-ACA-MCT)

Following Example 14 and replacing the thioacetic acid with methoxythioacetic acid (97.7 g, 0.8 mole) and using an identical analytical profile of the process, 86.3 g of the compound of the title were isolated, with an 80% yield. The infrared and proton magnetic resonance spectra are consistent with its structure.

$C_{11}H_{14}N_2O_5S_2$. Calculated: C,41,50; H,4,44; N,8,80; S,20,14; (318,36). Found: C,41,10; H,4,40; N,8,75; S,20,00.

EXAMPLE 17

7-amino-3-[(3-methoxy-pyridazin-6-yl)-thiomethyl]-3-cephem-4-carboxylic acid

Following Example 6 and replacing the thiazoline with 112 g of 3-methoxy-6-mercaptopyridazine, the compound of the title was isolated with a similar yield.

IR(KBr)$\nu$: 1800(beta-lactam), 1620(carboxylate), 1540($NH_3^+$, broad) cm$^{-1}$.

EXAMPLE 18

7-amino-3(5-methyl-1,3,4-thiadiazol-2-yl) thiomethyl-3-cephem-4-carboxylic acid (7-ACA-TD)

A mixture of 30 g of 5-methyl-2-mercapto,1,3,4-thiadiazole, 32 ml of triethylamine and 5 g of pivalic acid in 2 liters of water was heated to 82° C. Thereafter there was added in one shot 40 g of 7-aminocephalosporanic acid (92%) and 5 g of pivalic acid were added in one shot to the resulting solution. Precipitation started after a few minutes and increased with time. After 30 minutes of vigorous stirring at the same temperature, the mixture was cooled to 65° C. The solid was isolated by filtering, washed with water and acetone to give 35 g of the compound of the title. The liquors were cooled to 20° C. and filtered and gave a further 5 g fraction, with an overall yield of 87%. The infrared and proton magnetic resonance spectra are consistent with the technically pure product.

Analytical profile of the process:
1—pH of the thiadiazole, triethylamine and pivalic acid mixture solution at 82° C., 5,92.
2—pH of the solution containing 7-aminocephalosporanic acid and pivalic acid, 4.8.
3—Temperature of the solution containing 7-aminocephalosporanic acid, 82° C.
4—Reaction temperature, 82°–83° C.
5—Reaction isoelectric pH, 4.80–5.10.
6—Reaction time, 30 minutes.
7—Isolation temperature, 60° C. and 20° C.

What we claim is:

1. In a process for the preparation of a 3-substituted 7-aminocephalosporanic acid of the formula

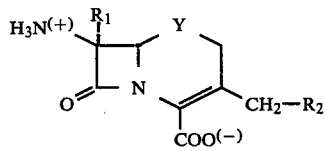

wherein $R_1$ is either hydrogen, methyl or methoxy; Y is either nitrogen, oxygen, sulphur or sulphoxide; $R_2$ is either azide or a radical of the formula:

$R_3$—S— wherein $R_3$ is either carbamoyl, $C_1$–$C_4$ alkoxycarbonyl, aryloxy, carbonyl, acetyl, phenylacetyl, benzoyl, thienyl, oxazolyl, thioxazolyl, thiadiazolyl, triazolyl, tetrazolyl, benzoxazolyl, pirazolyl, pyridyl, pirazinyl, pyrimidinyl, quinazoline, quinoline, benzimidazolyl, purinyl, pyridine-1-oxido-2-yl, pyridazine-1-oxido-6-yl, tetrazolylpyridizanilyl or thiatriazolyl, which may be substituted by either halogen, $C_1$–$C_4$ alkyl, phenyl, hydroxyl, amino, acetamido, nitro, cyano, acyloxy, carboxyl, N,N-dialkyl, $C_1$–$C_4$ sulphoalkyl, methoxy, sulphamoyl or carbamoyl, or one or more of said radicals;

said process having as starting compounds a 7-aminocephalosporanic acid represented by the formula

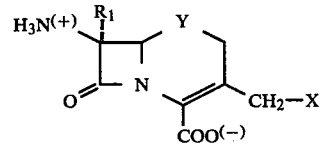

wherein $R_1$ and Y are as hereinbefore defined, and X is either chlorine, carbamoyloxy, or acetoxy; and a compound selected from the group consisting of sodium azide and a thiol compound represented by the formula $R_3$—SH wherein $R_3$ is as hereinbefore defined, the improvement comprising adding said starting compounds to an aqueous solution at a temperature of from about 20° to about 95° C., and at an isoelectric pH of from about 4.2 to about 5.9, said aqueous solution comprising water, a tertiary organic base selected from the group consisting of pyridine, methyl- or ethyl-substituted pyridine, $C_1$–$C_4$ tertiary alkylamino and bicyclic amidine selected from the group consisting of 1,5-diazobicyclic [5.4.0] undec-5-ene and 1,5-diazobicylic [4.3.0] non-5-ene, and a reaction isoelectric pH regulator selected from the group consisting of carbon dioxide, boric acid, trimethylacetic acid, 2-ethylhexanoic acid and an excess of a previously defined thiol compound; in which aqueous solution a reaction takes place between said starting 7-aminocephalosporanic acid in the zwitterion form and the ionic form $R_3\text{—}S^{(-)}$ of said thiol compound or the ionic form $N_3^{(-)}$ of said sodium azide, to obtain a mixture having a process pH analytical profile determined by a composition given by (a) the pH of the thiol and the tertiary organic base mixture, within the range of about 5.0 and 7.5; (b) the pH of the solution containing the 7-aminocephalosporanic acid, within the range of about 4.2 to about 5.9; (c) the reaction isoelectric pH, within the range of about 4.2 to about 5.9; and (d) the isolation pH, comprised between the isoelectric pH of the 3-substituted 7-aminocephalosporanic acid and the reaction isoelectric pH; the components of said mixture being reacted together at a process temperature determined by (a) the 7-aminocephalosporanic acid solution, within a range of about 50° to about 95° C.; (b) a temperature at the reaction isoelectric pH within the range of about 50° to about 85° C.; and (c) an isolation temperature within the range of about 20° to about 70° C.; and with a processing period of between about 15 to about 180 minutes; to obtain a 3-substituted 7-aminocephalosporanic acid of the previously defined formula.

* * * * *